(12) United States Patent
Passman (10) Patent No.: US 11,648,115 B2
(45) Date of Patent: May 16, 2023

(54) EXPANDABLE INTRODUCER SHEATH (71) Applicant: Edwards Lifesciences Corporation, Irvine, CA (US)

(72) Inventor: Joseph Arthur Passman, Costa Mesa, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 120 days.

(21) Appl. No.: 16/584,262

(22) Filed: Sep. 26, 2019

(65) Prior Publication Data

US 2020/0107931 A1  Apr. 9, 2020

Related U.S. Application Data

(60) Provisional application No. 62/740,690, filed on Oct. 3, 2018.

(51) Int. Cl.
*A61F 2/24* (2006.01)
*A61M 25/06* (2006.01)

(52) U.S. Cl.
CPC ........... *A61F 2/2436* (2013.01); *A61F 2/2433* (2013.01); *A61M 25/0662* (2013.01); *A61F 2/2418* (2013.01); *A61F 2210/0014* (2013.01)

(58) Field of Classification Search
CPC ............... A61F 2/2436; A61F 2/2433; A61F 2210/0014; A61F 2/2418; A61F 2/966; A61M 25/0662; A61M 2025/0024; A61M 25/0023; A61M 25/005
See application file for complete search history.

(56) References Cited

U.S. PATENT DOCUMENTS

| | | | |
|---|---|---|---|
| 5,395,341 A | 3/1995 | Slater | |
| 6,090,072 A | 7/2000 | Kratoska et al. | |
| 6,690,936 B1 | 2/2004 | Lundh et al. | |
| 7,927,309 B2 | 4/2011 | Palm | |
| 8,652,602 B1* | 2/2014 | Dolla | B29C 44/357 442/205 |
| 8,986,362 B2 | 3/2015 | Snow et al. | |
| 9,119,738 B2 | 9/2015 | Fish | |
| 9,192,751 B2 | 11/2015 | Macaulay et al. | |
| 9,555,214 B2 | 1/2017 | Ren et al. | |
| 9,801,657 B2 | 10/2017 | Furnish et al. | |
| 2005/0283228 A1* | 12/2005 | Stanford | A61F 2/915 623/1.15 |
| 2013/0281787 A1 | 10/2013 | Avneri et al. | |
| 2016/0095622 A1 | 4/2016 | Clancy et al. | |
| 2016/0296332 A1 | 10/2016 | Zhou et al. | |
| 2017/0014157 A1 | 1/2017 | Coyle et al. | |
| 2017/0281344 A1* | 10/2017 | Costello | A61M 25/0023 |
| 2018/0008407 A1 | 1/2018 | Maimon et al. | |
| 2018/0271654 A1* | 9/2018 | Hariton | A61F 2/243 |
| 2018/0325548 A1 | 11/2018 | Haverkost et al. | |

FOREIGN PATENT DOCUMENTS

WO    2019212814    11/2019

* cited by examiner

*Primary Examiner* — Brian A Dukert
(74) *Attorney, Agent, or Firm* — Rick Cates; Sean Seung Kyu Kim (57) ABSTRACT

A system for delivering medical implants has an expandable introducer sheath which can locally expand and lengthen to accommodate passage of a delivery catheter and implant, such as a prosthetic heart valve secured to a balloon catheter. The expandable sheath may be configured so that the local expansion is proportional to the local surface lengthening.

13 Claims, 7 Drawing Sheets

EXPANDABLE INTRODUCER SHEATH

CROSS REFERENCE TO RELATED APPLICATION

This application claims priority from U.S. Provisional Patent Application No. 62/740,690, filed Oct. 3, 2018, which is incorporated herein by reference in its entirety.

FIELD OF THE INVENTION

The present invention relates to systems and methods for delivering and deploying medical implants such as prosthetic heart valves, and, more particularly, to methods and apparatuses using an expandable sheath to accommodate implant delivery.

BACKGROUND OF THE INVENTION

Catheter systems, such as treatment, delivery, and/or deployment catheters, are used to treat patients internally. For example, delivery catheter systems are used to deliver and deploy prosthetic devices, such as prosthetic heart valves, at locations inside the body. Prosthetic heart valves can be delivered to a treatment site (e.g., aortic, mitral, tricuspid, and/or pulmonary valve position) within a patient using transcatheter techniques.

Introducer sheaths can be used to safely introduce delivery devices, such as delivery catheters, into a patient's vasculature using various approaches, such as a transfemoral approach via the femoral artery. Such introducer sheaths protect the local tissue and ease the introduction of the delivery catheter into the patient. A typical introducer sheath generally has an elongated sleeve that is inserted into the vasculature, and a housing that remains outside the patient and which contains one or more sealing valves that minimize blood loss out of the sheath as a delivery apparatus is advanced into the patient via the elongated sleeve and housing.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding access sheaths are known in the art. Such sheaths may have complex mechanisms, such as ratcheting mechanisms that maintain the sheath in an expanded configuration once a device with a larger diameter than the sheath's original diameter is introduced. Other sheaths can elastically deform, and can temporarily radially expand in an elastic fashion responsive to outward pressure caused by a delivery catheter or other device as it passes within the sheath. Some of these sheaths will elastically deform/radially expand in local areas as wider portions of the delivery catheter are passed therethrough, and then retract to a smaller (e.g., original) diameter when the wider parts of the delivery system have passed that particular portion of the sheath. However, the local radial expansion may create changes in the overall length of the sheath, which can cause portions of the sheath to change position in the patient's vasculature. Additionally, current expandable sheath technology fails to relieve compression along the entire length of the delivery catheter body, and can actually increase the sheath's compressive forces as the sheath is expanded. These compressive forces may interfere with advancement of the catheter/implant through the sheath, and/or require high delivery forces to advance the catheter/implant through the sheath.

There is a need for delivery sheaths which can locally radially expand to accommodate delivery catheters/devices without causing changes in the overall length of the sheath. There is also a need for delivery sheaths that relieve compression on the larger delivery catheter as the delivery catheter is passed through the sheath body. The current invention fulfills these needs.

SUMMARY OF THE INVENTION

The present invention provides systems, devices, and methods for accessing a patient's body using an access sheath and a delivery/deployment/treatment catheter, such as may be desired during heart valve implant procedures such as transcatheter heart valve delivery.

In one embodiment, a sheath is configured that can locally lengthen responsive to and proportional to corresponding local radial expansion, and/or vice versa, i.e., locally radially expand responsive to and proportional to corresponding local surface lengthening. The local surface lengthening permits the sheath overall length to remain constant during local radial expansion. The local radial expansion creates a larger diameter lumen that can accommodate larger structures, and may also provide for decreased compressive forces onto a catheter and/or implant passing through the sheath. The local surface lengthening may preferably occur in direct response to the local radial expansion, and without the need for the application of any other forces (other than the force(s) which caused the local radial expansion). The local radial expansion may preferably occur in direct response to the local surface lengthening, and without the need for the application of any other forces (other than the force(s) which caused the local surface lengthening).

Sheaths of the invention may exhibit a negative Poisson ratio. In prior expandable sheaths, the act of passing a delivery catheter within the sheath caused radial expansion of the sheath but also cause increased compressive forces by the sheath against the delivery catheter, typically leading to a need for increased insertion forces to advance the catheter through the sheath. By contrast, the sheath of the current invention has a negative Poisson ratio, where radial expansion of the sheath (which can be caused by longitudinal tensile forces and/or radially expansive forces) results in reduction of compressive forces from the sheath as the sheath expands. The reduction of compressive forces during radial expansion causes a decrease in the internal resistance of the sheath against advancement of the catheter/implant through the sheath. This lowers the overall force required to introduce and advance the delivery catheter/implant through the sheath, and may aid in reducing procedural complexity and also reduce the forces imposed on the patient's anatomy during the procedure.

The sheath may preferably be configured so that radial expansion and lengthening are proportional and interconnected with each other, such as where radial expansion is proportional to local surface lengthening, and/or where local surface lengthening is proportional to radial expansion. Radial expansion may be caused, in whole or in part, by lengthwise tensile forces locally along the sheath. For example, advancing a catheter through the sheath may cause lengthwise tensile forces locally on the sheath, which can cause local surface lengthening which in turn causes local radial expansion. Lengthening may be caused, in whole or in part, by radially outward forces along the length of the sheath. For example, expanding a device within the sheath may cause radially expansive forces locally on the sheath, which can cause radial expansion which in turn causes local surface lengthening.

Sheaths according to the invention may include a stent-like frame which provides desired expansion/lengthening/Poisson ratio performance. The stent-like frame may also provide improved kink resistance/performance, even at very small diameters and very small wall thicknesses.

The sheath of an embodiment of the invention has an insertion body and a hub, with the insertion body being elongated and configured for advancement into a patient, such as into a femoral artery. The sheath may have an outer elastic layer, an inner lining layer, and a stent-like frame between the inner and outer layers, and may also have adhesive to secure the layers/frame together. The stent-like frame may be configured to locally radially expand responsive to local surface lengthening of the stent-like frame, and/or to locally lengthen responsive to local radially expansion. The sheath may be configured to slidingly receive a catheter therein (such as a delivery catheter with implant thereon) and to radially expand and lengthen locally responsive to the catheter being slidingly advanced through the sheath.

The stent-like frame of a sheath may have a plurality of circumferential links, a plurality of nodes, and a plurality of longitudinal links, with a plurality of ring-like elements extending about a circumference of the stent-like frame, each ring-like element comprising circumferential links ring-like elements alternating with nodes and extending circumferentially about the ring-like element. Adjacent ring-like elements may be secured to each other via longitudinal links extending longitudinally between and connecting the nodes of the adjacent ring-like elements. In an unexpanded and unlengthened configuration of the stent-like frame the longitudinal links and circumferential links have more-curved shapes, and in an expanded and lengthened configuration of the stent-like frame the longitudinal links and circumferential links have less-curved shapes.

Expansion of the stent-like frame may cause the circumferential links to at least partially straighten, which causes the nodes to at least partially rotate, which causes the longitudinal links to at least partially straighten. Lengthening of the stent-like frame may cause the longitudinal links to at least partially straighten, which causes the nodes to at least partially rotate, which causes the circumferential links to at least partially straighten.

A system for delivering a prosthetic heart valve within a native valve annulus of a patient according to an embodiment of the invention includes an introducer sheath, a delivery catheter configured to be advanced through a patient internal vessel, and an implant secured to the delivery catheter.

Methods of the invention for treating a patient, such as by delivering a heart valve repair implant within the heart of a patient, may include: creating an incision in the patient leading from an access site on and outer skin surface of the patient and into a first blood vessel; advancing a distal end of an access sheath through the incision and into the first blood vessel, wherein the access sheath is configured to locally radially expand and locally lengthen as a catheter and implant are advanced therethrough; advancing a guide wire from the access site thru the incision and access sheath and the first blood and to a position at or adjacent a treatment site; advancing a catheter distal end along the guide wire to the treatment site, wherein advancing the catheter comprises locally expanding and locally lengthening the access sheath responsive to advancement of the catheter therethrough; applying treatment at the treatment site via the catheter; removing the catheter from the patient; removing the guide wire from the patient; removing the access sheath from the patient; and closing the incision. The first blood vessel may be a femoral artery, and the distal end of the access sheath may be advanced into the aorta. The treatment site may be at or adjacent a heart valve. The catheter may be a delivery catheter having a prosthetic heart valve at the catheter distal end. Locally lengthening the access sheath may be caused by tension applied longitudinally to the access sheath by advancement of the catheter, and locally expanding the access sheath is caused by locally lengthening the access sheath. The systems, devices, and/or methods of the present invention can be utilized in various catheter-based procedures, including minimally-invasive procedures and percutaneous procedures. In some embodiments the methods/systems/devices may involve transapical deliveries through a small chest incision. In other embodiments, the methods/systems/devices can be used in transatrial procedures. In yet other embodiments, the methods/systems/devices can be used in percutaneous procedures, such as via a catheter or catheters into the patient's arterial system (e.g., through the femoral or brachial arteries).

It should be understood that each of the elements disclosed herein can be used with any and all of the elements disclosed herein, even though the specific combination of elements may not be explicitly shown in the figures herein. In other words, based on the explanation of the particular device, one of skill in the art should have little trouble combining the features of certain of two such devices. Therefore, it should be understood that many of the elements are interchangeable, and the invention covers all permutations thereof.

Other objects, features, and advantages of the present invention will become apparent from a consideration of the following detailed description.

DETAILED DESCRIPTION OF SEVERAL EMBODIMENTS

Figure 1:
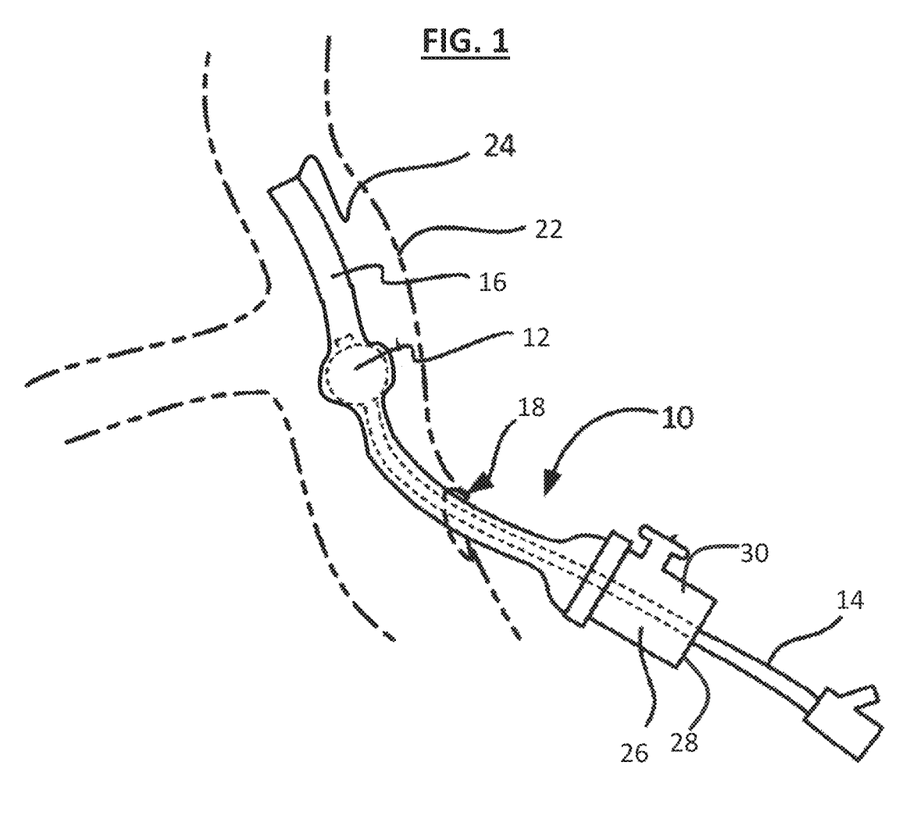
FIG. 1 is a side view of a system delivering a device via a catheter to a position in a patient according to an embodiment of the invention.
Figure 2A:
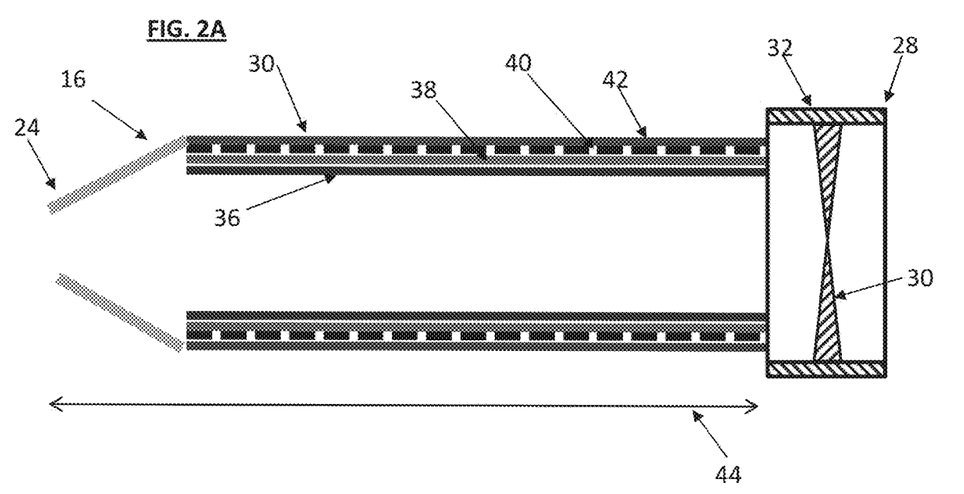
FIGS. 2A and 2B depict side and end views (in cross section) of a sheath according to an embodiment of the invention.
Figure 2B:
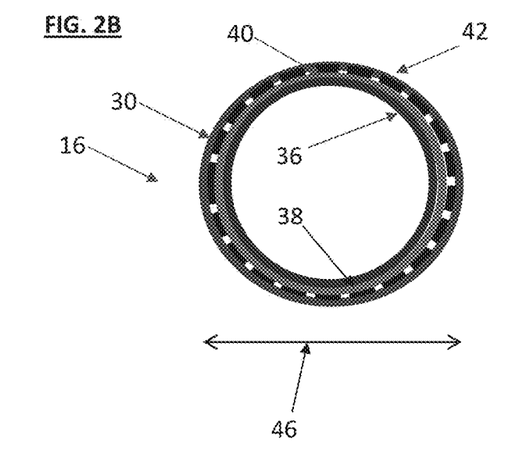

FIG. 1 illustrates a system 10 according to the present invention for delivering and deploying a prosthetic heart valve 12 or another medical device at a desired site in a patient. The system 10 includes a delivery catheter 14 (such as a balloon catheter) with prosthetic heart valve thereon being advanced through a delivery sheath 16. Generally, sheath 16 is passed through an incision 18 in the patient and into a vessel 22, such as the transfemoral blood vessel, such that the distal end 24 of the sheath 16 is inserted into the vessel 22. Sheath 16 can include a hub 26 at a sheath proximal end 28, with a hemostasis valve 30 contained within the hub 26 to prevent body fluid loss through the hub 26. The delivery catheter 14 with prosthetic valve 12 thereon can be inserted into and advanced through the sheath 16 in order to advance and position the prosthetic device 12 at a desired treatment location in the patient. A sheath 16 according to an embodiment of the invention is depicted in FIGS. 2A-2C. The sheath 16 has a distal end 24 and proximal end 28, with an elongated insertion body 32 and a hub 26. A sheath lumen 34 passes through sheath 16 from the proximal end 28 to the distal end 24.

The elongated insertion body 32 of the sheath 16 may be formed of a multi-layer construction. In the particular embodiment depicted, a low-friction liner 36 (such as PTFE, FEP, PEBAX, etc., which may be compounded with lubricious materials, e.g., PEBAX with PROPEL) is provided which defines the walls of the sheath lumen 34. The low-friction liner 36 facilitates the advancement of catheters and other devices through the sheath 16. A layer of adhesive 38 may be provided, such as a tie-layer adhesive. A stent-like frame 40 may provide desired expansion/retraction characteristics. An elastomeric jacket 42 may enclose the sheath exterior. Note that with respect to the liner 36, adhesive 38, stent-like frame 40, and jacket 42, an insertion body 32 according to the invention may include all, none, or any combination of these elements. For example, a stent-like frame 40 may be used, but without the use of an inner liner 36, adhesive 38, and/or outer jacket/liner 42. The entire insertion body 32 is configured so that it can locally expand in a radial fashion but still maintain a constant length of the overall insertion body length by causing a local surface length extension in the wall portion of the insertion body 32 to accommodate local distortions in the wall portion caused by the radial expansion. The insertion body 32 may preferably have a length 44 sufficient to permit the sheath distal end 24 to be extended to a desired location in the patient (e.g., a desired location in a blood vessel, such as in an ascending aorta where the access is made via a transfemoral approach) while the hub 26 remains outside of the patient.

Lengths 44 that are within the scope of the invention include 12-18 inches (30-45 cm), 14-16 inches (35 to 40 cm), etc. (for transfemoral approaches), although other lengths are also within the scope of the invention depending on the particular application. The insertion body 32 may have an initial outer diameter 46A small enough to easily fit through the access point, target blood vessel (e.g., the aorta), and any intervening body features (e.g., femoral artery). Initial (unexpanded) outer diameters that are within the scope of the invention include 3-8 mm for transfemoral procedures, although other lengths are also within the scope of the invention depending on the particular application. During expansion, the sheath's outer diameter may potentially expand by 20% (or more), 30% (or more), 40% (or more), or even 50% (or more).

Figure 3A:
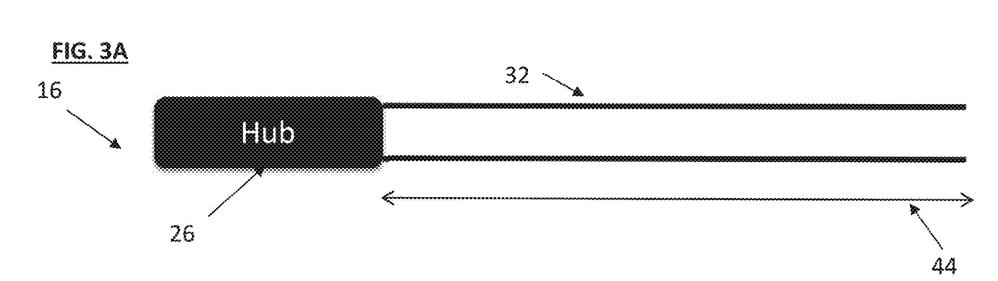
FIGS. 3A-3C depict side views of a system during transcatheter device delivery through the sheath according to an embodiment of the invention.
Figure 3B:
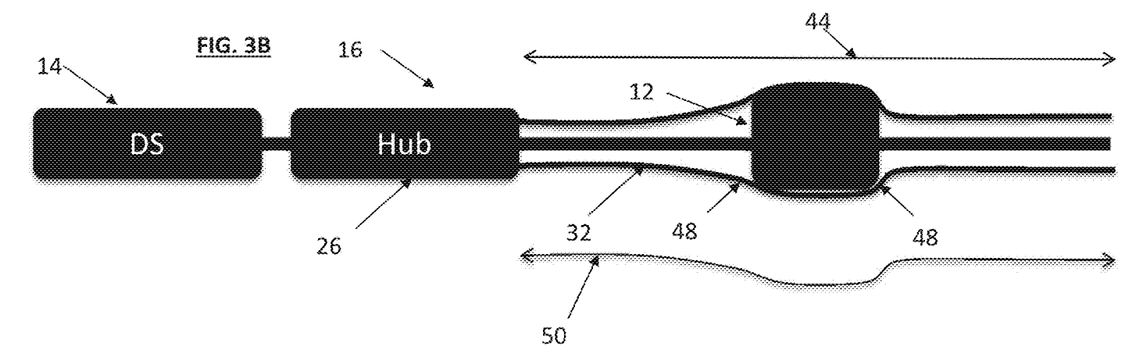
Figure 3C:
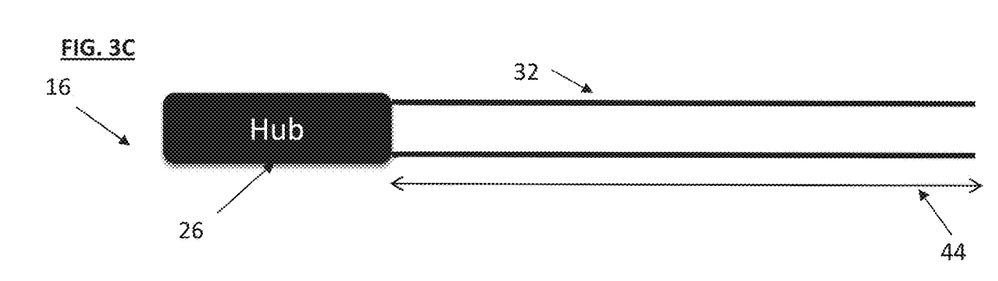

FIGS. 3A-3C depict a sheath 16 according to the invention having an insertion body portion 32 which locally expands both radially and lengthwise during catheter advancement while maintaining the same overall insertion body length 44. As shown in FIG. 3A, prior to advancement of a catheter and implant through the sheath 16, the insertion body portion 32 of the sheath 16 has a diameter 46 and an overall length 44. As a delivery catheter 14 with implant 12 (e.g., prosthetic heart valve) thereon is advanced through the sheath 16, as depicted in FIG. 3B, the insertion body portion 32 is locally expanded in a radial fashion around the implant 12. As the sheath/insertion body portion 32 is expanded, the compressive forces of the sheath/insertion body portion are reduced due to the negative Poisson ratio of the stent-like frame 40 during radial expansion. This reduction in compressive forces translates to less resistance from the sheath to advancement of the catheter/implant through the sheath.

The local radial expansion causes contour distortions along the exterior surface of the insertion body portion 32, such as at the "shoulders" 48 created on the insertion body portion 32 at either side of the implant 12. These surface distortions would result in an overall shortening of the sheath if they were not accompanied by local surface lengthening of the sheath exterior surface. As shown in FIG. 3B, the local surface lengthening provides a surface distance or contour length 50 (i.e., the distance along the surface of the insertion body portion) which is longer than the "linear" overall length 44 of the sheath insertion portion 32. The result is that the overall length 44 of the sheath insertion portion 32 remains constant as the surface distance/contour length 50 of the sheath surface varies to accommodate the radial expansion of the sheath 16. As depicted in FIG. 3C, after the catheter and implant are removed from the sheath 16, the insertion portion 32 returns to its original diameter.

Figure 4A:
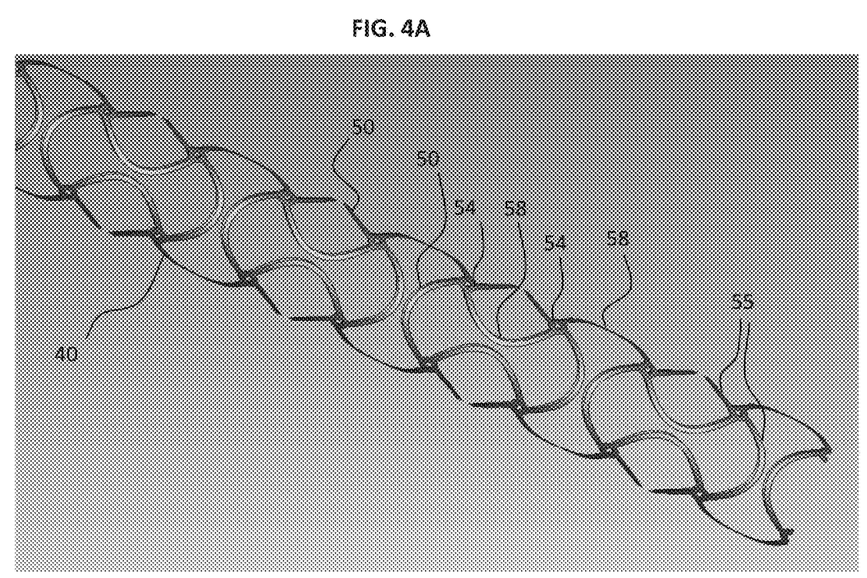
FIGS. 4A and 4B depict perspective views of a stent-like frame according to an embodiment of the invention.
Figure 4B:
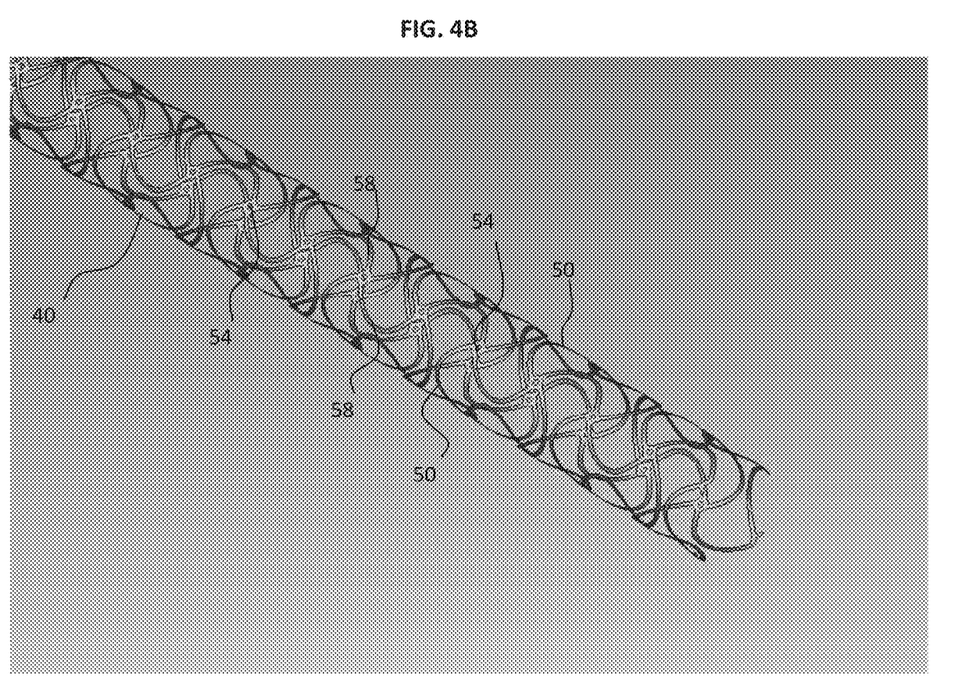

FIGS. 4A-4B show a stent-like frame 40 for use with a sheath 16 according to an embodiment of the invention. The stent-like frame 40 has a series of circumferentially-extending links 50 having circumferential link ends 52 secured to nodes 54 to form ring-like elements 55 extending radially around the stent-like frame, and longitudinally-extending links 56 having longitudinal link ends 58 secured to the nodes 54 such that the longitudinally-extending links 56 connect adjacent ring-like elements 55. Each node is secured to a total of four (4) links, with two (2) circumferential link ends 52 secured to opposing sides of each node 54 and two (2) longitudinal link ends 58 secured to opposing sides of each node 54. The specific structure of nodes 54 and links 50, 52 can result in a frame 40 in which local radial expansion inherently causes a corresponding local surface length extension, but where the structure causes the stent-like frame 40 to return to its original surface length when it returns to its original diameter. The reverse may also be true, where the specific structure of nodes 54 and links 50, 52 can result in a frame 40 in which local surface lengthening inherently causes a corresponding local radial expansion, but where the structure causes the stent-like frame 40 to return to its original diameter when it returns to its original surface length.

The embodiment of FIGS. 4A-4B is just one example of a specific geometry in accordance with the invention. Note that other stent-like frame configurations which accomplish the desired negative Poisson ratio are also within the scope of the invention. Also, stent-like frames of the invention may be formed from various materials. For example, the frame 40 may be formed of a memory material such as nitinol that permits the sheath to locally expand/lengthen responsive to the outward pressure caused by the catheter and implant being advanced though the sheath, and then returns to its original diameter/local surface length once the catheter/implant have cleared the sheath.

Figure 5A:
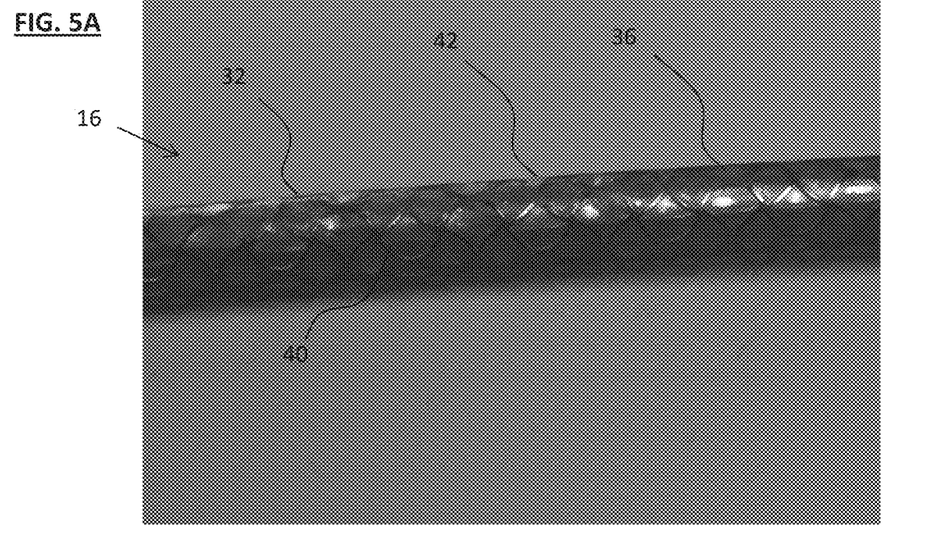
FIG. 5A depicts a side view of a sheath which includes a stent-like frame such as the frame depicted in FIGS. 4A and 4B.
Figure 5B:
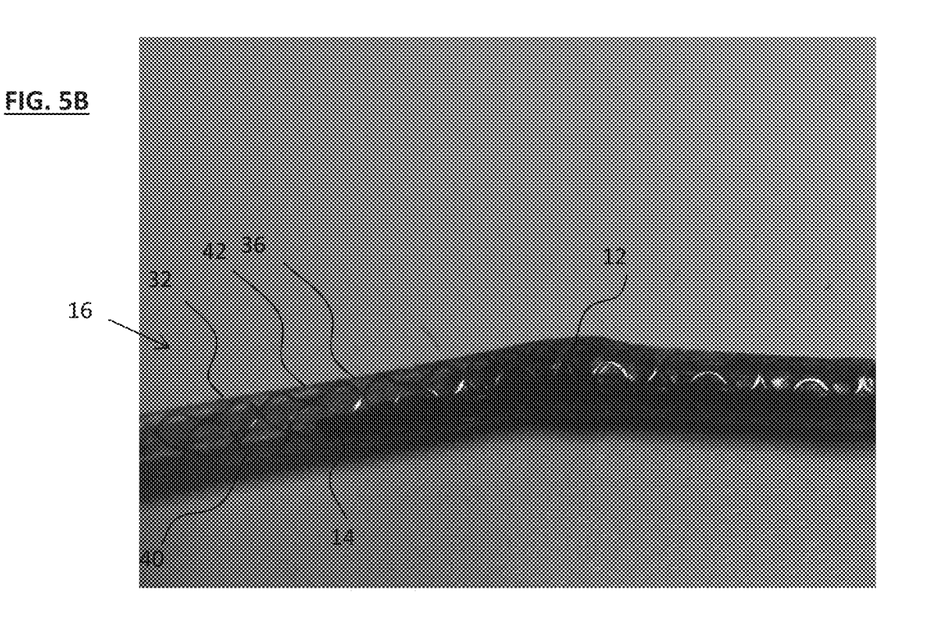
FIG. 5B depicts a side view of the sheath of FIG. 5A with a delivery catheter being advanced therethrough.

FIGS. 5A and 5B depict an insertion portion 32 of a sheath 16 which includes a stent-like frame 40 such as that depicted in FIGS. 4A-4B, with the other layers (e.g., inner liner 36, elastomeric jacket 42, etc.) in the particular embodiment depicted being relatively transparent so that the frame 40 can be seen. As a delivery catheter 14 and implant 12 are advanced through the sheath 16, as shown in FIG. 5B, the insertion portion 32 and stent-like frame 40 locally deform, including radially expansion and lengthening locally, to accommodate the catheter 14 and implant 12, while maintaining the overall sheath length.

Figure 6A:
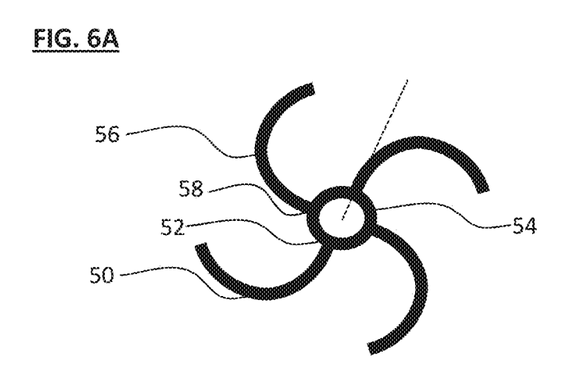
FIGS. 6A and 6B depict operational characteristics of a node portion of a stent-like frame for use with a sheath according to an embodiment of the invention.
Figure 6B:
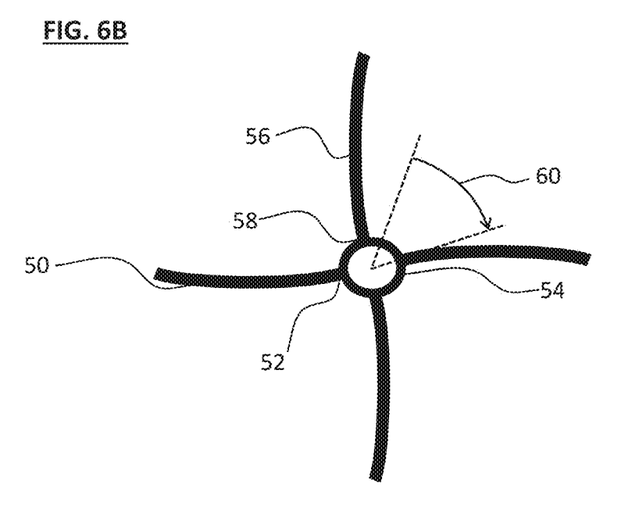

The operational characteristics of a general node-and-link design of the invention involve specific interactions between respective links and nodes. As shown in FIG. 6A, prior to local expansion and lengthening the circumferential links 50 and longitudinal links 56 have pronounced curves. If radially outward forces or other forces cause radial expansion, as the radial expansion occurs, the circumferential links 50 are stretched into a less curved/more straight configuration. As the circumferential links 50 are stretched and straightened, the circumferential link ends 52 transfer force against the nodes 54 and cause a rotational moment on the nodes 54. The rotational moment causes the nodes 54 to rotate through an angle 60, which in turn causes the rotational moment to be transferred through the node 54 and into the longitudinal link ends 58 to rotate same, thus causing the longitudinal links 56 to at least partially straighten. The at least partial straightening of the longitudinal links 56 causes local surface lengthening of the stent structure, as shown in FIG. 6B. Similarly, if longitudinal tensile forces or other lengthening-inducing forces cause local surface lengthening, as the surface lengthening occurs the longitudinal links 56 are stretched into a less curved/more straight configuration. As the longitudinal links 56 are stretched and straightened, the longitudinal links ends 58 transfer force against the nodes 54 and cause a rotational moment on the nodes 54. The rotational moment causes the nodes 54 to rotate through an angle 60, which in turn causes the rotational moment to be transferred through the node 54 and into the circumferential link ends 52 to rotate same, thus causing the circumferential links 50 to at least partially straighten. The at least partial straightening of the circumferential links 50 causes local radial expansion of the stent structure, as shown in FIG. 6B.

Note that the angle 60 through which the node is rotated may be relatively large. For example, the angle could be 30 to 60 degrees, 30 to 90 degrees, 30 degrees (or more), 45 degrees (or more), 60 degrees (or more), or even 90 degrees (or more).

Figure 7A:
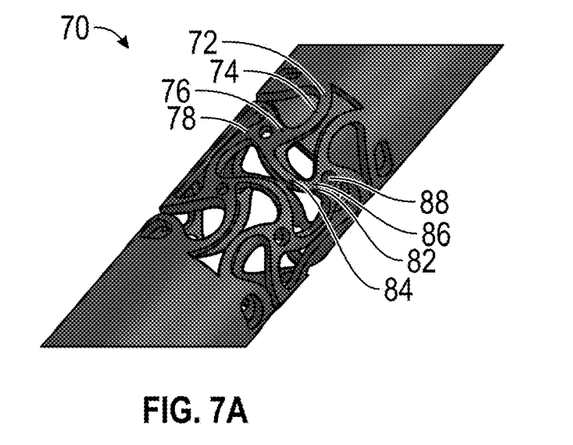
FIGS. 7A-7C depict a stent-like frame portion in an unexpanded condition, partially expanded condition, and fully expanded condition, respectively, according to an embodiment of the invention.
Figure 7B:
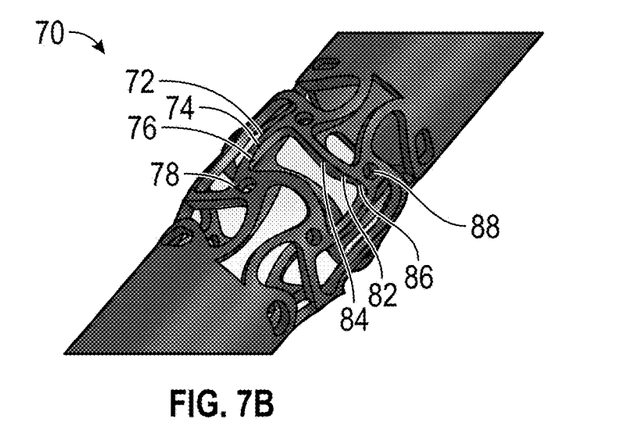
Figure 7C:
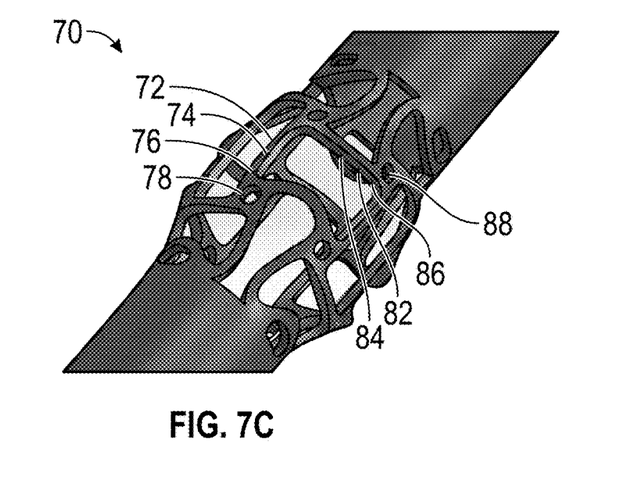

A specific stent-like frame portion 70 as depicted in FIGS. 7A-7C includes longitudinal links 72 having thinner center portions 74 and wider end portions 76 where the link is secured to a node 78. Similarly, circumferential links 82 having thinner center portions 84 and wider end portions 86 where the link is secured to a node 78. The combination of thinner center portions and wider end portions makes it easier for the links 72, 82 to bend into straighter forms in their center portions 74, 84, while making it more difficult for the links 72, 82 to bend at or adjacent the end portions 76, 86 at the points the links 72, 82 are secured to the nodes 78. The result is that rotational moments are more easily transferred into and out of the nodes 78 via the links 72, 82 as the links are straightened.

Nodes 78 according to the invention may include internal cutouts, such as the circular cutouts 88 depicted in FIGS. 7A-7C. The circular cutouts 88 reduce the mass of the node 78 and also of the overall stent frame. The reduction in node mass reduces the rotational moment of inertia of each node 78, making it easier for each node 78 to rotate and to transfer rotational moments from circumferential links 82 to longitudinal links 72 and vice-versa.

The stent-like frame 40 is depicted in FIG. 7A in its pre-expansion, pre-lengthened form. Note that the stent-like frame may be may formed in various ways, such as by being laser cut or otherwise cut from a tube (such as a metal tube, e.g., nitinol tube). As a portion of the stent-like frame is expanded, as depicted in FIG. 7B, the straightening out of the circumferential links 82 cause the nodes 78 to rotate and thereby cause the longitudinal links 72 to bend to a more straightened configuration. Similarly, as a portion of the stent-like frame is lengthened, as depicted in FIG. 7B, the straightening out of the longitudinal links 72 cause the nodes 78 to rotate and thereby cause the circumferential links 82 to bend to a more straightened configuration. As depicted in FIG. 7C, when fully expanded the nodes 78 are rotated even further, and the circumferential links 82 and longitudinal links 72 are almost completely straight—thereby resulting in local radial expansion combined with proportional local surface lengthening.

Various approaches for treatments, including advancing the catheters into position via the sheath, are within the scope of the invention. One preferred approach (e.g., when treating an aortic valve) is a transcatheter approach via a femoral artery. The method may include deployment of a transcatheter aortic valve replacement (TAVR), which may be performed using the same transcatheter approach.

In one example of a procedure according to the invention to deploy a prosthetic aortic heart valve according to the invention, femoral artery access is obtained via the access sheath of the invention which is dimensioned for use in TAVR procedures. An incision is created in the patient, leading to an internal blood vessel such as a femoral artery. The distal end of the access sheath is advanced through the incision and femoral artery and into a desired position within the aorta, with the hub positioned just outside the patient adjacent the incision/access site. A guide wire is advanced from the femoral access site thru the aortic arch and into the patient's left ventricle. The steerable shaft of the imaging catheter and/or delivery catheter can be advanced over the guide wire, such as via standard over-the-wire techniques, to advance the distal end of the device to the target location. For example, the device may have a guide wire lumen. Echo and/or fluoroscopic and/or other visualization techniques may be used as well as the electrophysiological 3D mapping techniques. The treatment and/or implant deployment can occur, such as by deploying the prosthetic heart valve at the target location. Once the proper deployment is confirmed, the catheter can be removed from the patient, the guidewire can be removed from the patient, the sheath can be removed from the patient, and the incision(s) closed, such as via sutures.

Note that each element of each embodiment and its respective elements disclosed herein can be used with any other embodiment and its respective elements disclosed herein.

All dimensions listed are by way of example, and devices according to the invention may have dimensions outside those specific values and ranges. The dimensions and shape of the device and its elements depend on the particular application.

Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise.

The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein, and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

What is claimed is:

1. A system for delivering a prosthetic heart valve to a native valve annulus of a patient, comprising:
    an introducer sheath comprising an insertion body and a hub, the insertion body comprising an outer elastic layer, an inner lining layer, and a stent-like frame between the inner and outer layers, the stent-like frame comprising a plurality of ring-like elements and a plurality of longitudinally-extending links, each of the plurality of longitudinally-extending links comprising a thinner center portion and a plurality of wider end portions, each ring-like element comprising a plurality of circumferentially-extending links alternating with a plurality of nodes, a longitudinally-extending link of the plurality of longitudinally-extending links extending between two nodes of two adjacent ring-like elements, and a node of a portion of the stent-like frame in an expanded state being rotated relative to the node of the portion in an unexpanded state to locally radially expand the stent-like frame responsive to local surface lengthening of the stent-like frame;
    a delivery catheter configured to be advanced through a patient internal vessel; and
    an implant secured to the delivery catheter;
    wherein the introducer sheath is configured to slidingly receive the delivery catheter with implant thereon and to radially expand and lengthen locally responsive to the delivery catheter with implant thereon being slidingly advanced through the introducer sheath.

2. The system of claim 1, wherein while the portion of the stent-like frame is in the unexpanded state, the longitudinally-extending links and circumferentially-extending links have more-curved shapes than while the portion of the stent-like frame is in the expanded state.

3. The system of claim 2, wherein the node is rotated between 30 degrees to 90 degrees while the portion of the stent-like frame is in the expanded state relative to its position while the portion of the stent-like frame is in the unexpanded state.

4. The system of claim 3, wherein the portion of the stent-like frame in the expanded state comprises a surface length longer than the portion in the unexpanded state.

5. The system of claim 4, wherein the portion of the stent-like frame in the expanded state comprises a linear length that is the same as that of the portion of the stent-like frame in the unexpanded state.

6. The system of claim 2, wherein the node is rotated between 30 degrees to 60 degrees while the portion of the stent-like frame is in the expanded state relative to its position while the portion of the stent-like frame is in the unexpanded state.

7. The system of claim 6, wherein the portion of the stent-like frame comprises the same linear length while the portion is in the expanded state and the unexpanded state.

8. The system of claim 7, wherein the stent-like frame comprises the same overall linear length while the portion of the stent-like frame is in the expanded state and the unexpanded state.

9. The system of claim 1, wherein each of the plurality of circumferentially-extending links comprises thinner center portions and wider end portions.

10. The system of claim 1, wherein each of the plurality of nodes comprises an internal cutout.

11. The system of claim 10, wherein the internal cutout comprises a circular cutout.

12. The system of claim 1, wherein two circumferentially-extending link ends are secured to opposing sides of each node.

13. The system of claim 1, wherein two longitudinally-extending link ends are secured to opposing sides of each node.

* * * * *